United States Patent
Won

(10) Patent No.: US 11,266,354 B2
(45) Date of Patent: Mar. 8, 2022

(54) METHOD OF GENERATING RESPIRATORY STATUS CLASSIFIER AND METHOD OF DETERMINING RESPIRATORY STATUS

(71) Applicant: INDUSTRY FOUNDATION OF CHONNAM NATIONAL UNIVERSITY, Gwangju (KR)

(72) Inventor: Yong Gwan Won, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 328 days.

(21) Appl. No.: 16/438,839

(22) Filed: Jun. 12, 2019

(65) Prior Publication Data

US 2019/0374167 A1 Dec. 12, 2019

(30) Foreign Application Priority Data

Jun. 12, 2018 (KR) .................. 10-2018-0067491

(51) Int. Cl.
  *G16H 50/20* (2018.01)
  *A61B 5/00* (2006.01)
  *A61B 5/08* (2006.01)

(52) U.S. Cl.
  CPC .......... *A61B 5/7267* (2013.01); *A61B 5/0803* (2013.01); *A61B 5/4818* (2013.01); *A61B 5/743* (2013.01); *G16H 50/20* (2018.01)

(58) Field of Classification Search
  CPC ... A61B 5/7267; A61B 5/0803; A61B 5/4818; A61B 5/743; G16H 50/20
  See application file for complete search history.

(56) References Cited

U.S. PATENT DOCUMENTS

2017/0215772 A1* 8/2017 Garn .................. A61B 5/08

FOREIGN PATENT DOCUMENTS

CA 2812678 A1 * 10/2013 ............. G16H 15/00

OTHER PUBLICATIONS

Shokrollahi, Mehrnaz, et al. "Snoring sound classification from respiratory signal." 2016 38th Annual International Conference of the IEEE Engineering in Medicine and Biology Society (EMBC). IEEE. (Year: 2016).*

* cited by examiner

*Primary Examiner* — Patrick Fernandes
*Assistant Examiner* — Liam A Wallace
(74) *Attorney, Agent, or Firm* — Studebaker & Brackett PC

(57) ABSTRACT

Provided are a method of generating a respiratory status classifier and a method of determining respiratory status. The method of generating a respiratory status classifier includes segmenting collected respiratory signals according to respiratory cycles, acquiring data pairs of a calculated power spectrum of frequency components and a designated respiratory status indication value for a plurality of cycle-specific respiratory signals selected from among the segmented cycle-specific respiratory signals, selecting specific frequency components from among the frequency components, inputting data pairs of a power spectrum and a designated respiratory status indication value corresponding to the specific frequency components to a respiratory status classifier, and training the respiratory status classifier according to output values from the classifier.

11 Claims, 5 Drawing Sheets

METHOD OF GENERATING RESPIRATORY STATUS CLASSIFIER AND METHOD OF DETERMINING RESPIRATORY STATUS

CROSS-REFERENCE TO RELATED APPLICATION

This application claims priority to and the benefit of Korean Patent Application No. 10-2018-0067491, filed on Jun. 12, 2018, the disclosure of which is incorporated herein by reference in its entirety.

BACKGROUND

1. Field of the Invention

The present invention relates to a method of generating a respiratory status classifier and a method of determining respiratory status, and more particularly, to a method of generating a respiratory status classifier for determining respiratory status through a respiratory signal by analyzing the respiratory signal and a method of determining respiratory status through the respiratory status classifier.

2. Discussion of Related Art

Sleep apnea causes breathing to stop frequently during sleep and triggers a sleep disorder such as severe snoring and daytime lethargy.

Snoring and sleep apnea are known as major factors causing mental diseases, such as depression and suicidal impulses, cardiovascular diseases, kidney diseases, cerebral infarction, cancer, sexual dysfunction, etc. and also cause accidents by drowsy driving, drowsy working, and the like. Therefore, it is important to accurately diagnose snoring and sleep apnea.

According to the prior art, an apparatus and method for examining sleep apnea using a piezoelectric sensor were disclosed. There is a configuration for simultaneously extracting a snoring signal and a heartbeat signal using a piezoelectric sensor and detecting obstructive sleep apnea (OSA) using the extracted snoring signal and heartbeat signal.

However, the prior art merely discloses a configuration for determining whether a person has sleep apnea on the basis of a sensing value measured by a piezoelectric sensor and discloses neither a method of generating a respiratory status classifier by collecting respiratory sound signals of subjects and training the respiratory status classifier with the collected signals nor a method of determining respiratory status using a generated respiratory status classifier.

SUMMARY OF THE INVENTION

The present invention is directed to providing a method of generating a respiratory status classifier having a small amount of calculation and high accuracy and a method of determining respiratory status using the generated respiratory status classifier in which respiratory sound signals collected from multiple unspecified sleeping people are divided into respiratory cycles, some or all of respiratory signals corresponding to each respiratory cycle and respiratory status indication values corresponding to the respiratory signals are paired to build a database, only frequency components useful for respiratory status classification are selected from cycle-specific respiratory signals, the respiratory status classifier is trained on the basis of a power spectrum and respiratory status indication values of the selected frequency components, and then the trained respiratory status classifier is used to determine the respiratory status of a continuously input respiratory sound signal in each respiratory cycle.

The present invention is directed to provide a low-computation and high accuracy design of sleep respirator status classifier and its real-time application for sleep respiratory status monitoring. The respiratory sound signals collected by piezo-electric sensors from multiple unspecified sleep people are segmented into respiratory cycles. Each respiratory cycle is labelled with corresponding status indication as normal, snoring or apnea stages. Pairs of each respiratory cycle and its corresponding respiratory status value are used to build a sleep respiratory sound database. However, only competitive frequency features in term of power spectrum and their corresponding label from each cycle-segmented respiratory signal are used to train the classifier. The trained classifier is then used to determine respiratory status of each respiratory cycle in a continuous sleep respiratory sound input signal.

According to an aspect of the present invention, there is provided a method of generating a respiratory status classifier, the method including: segmenting collected respiratory signals according to respiratory cycles; acquiring data pairs of a power spectrum of frequency components and a designated respiratory status indication value for each of respiratory signals corresponding to a plurality of selected respiratory cycles among the segmented cycle-specific respiratory signals; selecting specific frequency components from among the frequency components; and training a respiratory status classifier using data pairs of a power spectrum value of the selected specific frequency components and the designated respiratory status indication value.

The acquiring of the data pairs may be performed on one of the collected respiratory signals and then repeatedly performed on other respiratory signals until a specific condition is satisfied.

The acquiring of data pairs may include: calculating a power spectrum of frequency components for a respiratory signal corresponding to one respiratory cycle and designating a respiratory status indication value for the respiratory signal corresponding to the respiratory cycle to acquire a data pair of the respiratory signal corresponding to the respiratory cycle; and until a specific condition is satisfied, repeatedly acquiring a data pair of each of respiratory signals corresponding to the respiratory cycles except the respiratory cycle whose data pair has been acquired.

In the acquiring of data pairs, the power spectrums of the frequency components included in the data pairs may be normalized values.

The respiratory status indication value may include an indication value of a normal respiratory state, a snoring state, or an apnea state.

The respiratory status indication value may further include indication values for representing a level of the snoring state and a level of the apnea state in numbers, text, or symbols.

The selecting of specific frequency components may include: generating a decision tree classifier for classifying respiratory signals corresponding to the respiratory cycle according to the respiratory status indication values using the frequency components included in the data pair as input feature and using the power spectrum value of the frequency components as values of the input feature; and selecting only frequency components constituting a root node and an internal node of the generated decision tree classifier as the specific frequency components.

The generating of a decision tree classifier may include generating the decision tree classifier by repeatedly expanding the single internal node according to respiratory status indication values designated for data pairs allocated to the internal node until a ratio of data pairs belonging to one respiratory status to the data pairs becomes a preset ratio or more.

The training of the respiratory status classifier may include: inputting the power spectrums of the selected specific frequency components and the designated respiratory status indication values to the respiratory status classifier; and calculating errors by comparing output values from the respiratory status classifier with the designated respiratory status indication values, and adjusting parameters of the respiratory status classifier to reduce the calculated errors.

The training of the respiratory status classifier may be finished when the training is repeatedly performed a preset number of times or the calculated errors are less than or equal to a preset reference.

According to another aspect of the present invention, there is provided a method of determining respiratory status, the method including: separating a one-cycle respiratory signal from collected respiratory signals; inputting power spectrums of the specific frequency components selected in claim 1 among power spectrums of the separated one-cycle respiratory signal to the respiratory status classifier generated according to the method of claim 1; and determining the respiratory status of the separated one-cycle respiratory signal according to output values of the respiratory status classifier based on the inputs.

The method may further include, after the determining of respiratory status, repeating the separating of a one-cycle respiratory signal to the determining of respiratory status for a respiratory signal continuous to the separated one-cycle respiratory signal.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

The terms "first," "second," and/or the like are only used to distinguish one element from another element. In other words, the terms are not intended to limit elements.

Throughout this specification, the terms "include," "have," or the like, when used herein, specify the presence of corresponding elements, features, and steps but do not preclude the presence or addition of one or more elements, features, steps, and equivalents thereof.

As used herein, the singular form includes the plural form unless the context clearly indicates otherwise. In other words, an element and the like mentioned herein may indicate the presence or addition of one or more other elements and the like.

Unless otherwise defined, all terms including technical and scientific terms used herein have the same meaning as commonly understood by those of ordinary skill in the technical field to which the present invention pertains.

In other words, terms, such as those defined in commonly used dictionaries, should be interpreted as having a meaning that is consistent with their meaning in the context of the relevant art and are not to be interpreted in an idealized or overly formal sense unless expressly so defined herein.

Hereinafter, a method of training a respiratory status classifier and a method of determining respiratory status according to exemplary embodiments of the present invention will be described in detail with reference to the accompanying drawings.

Figure 1:
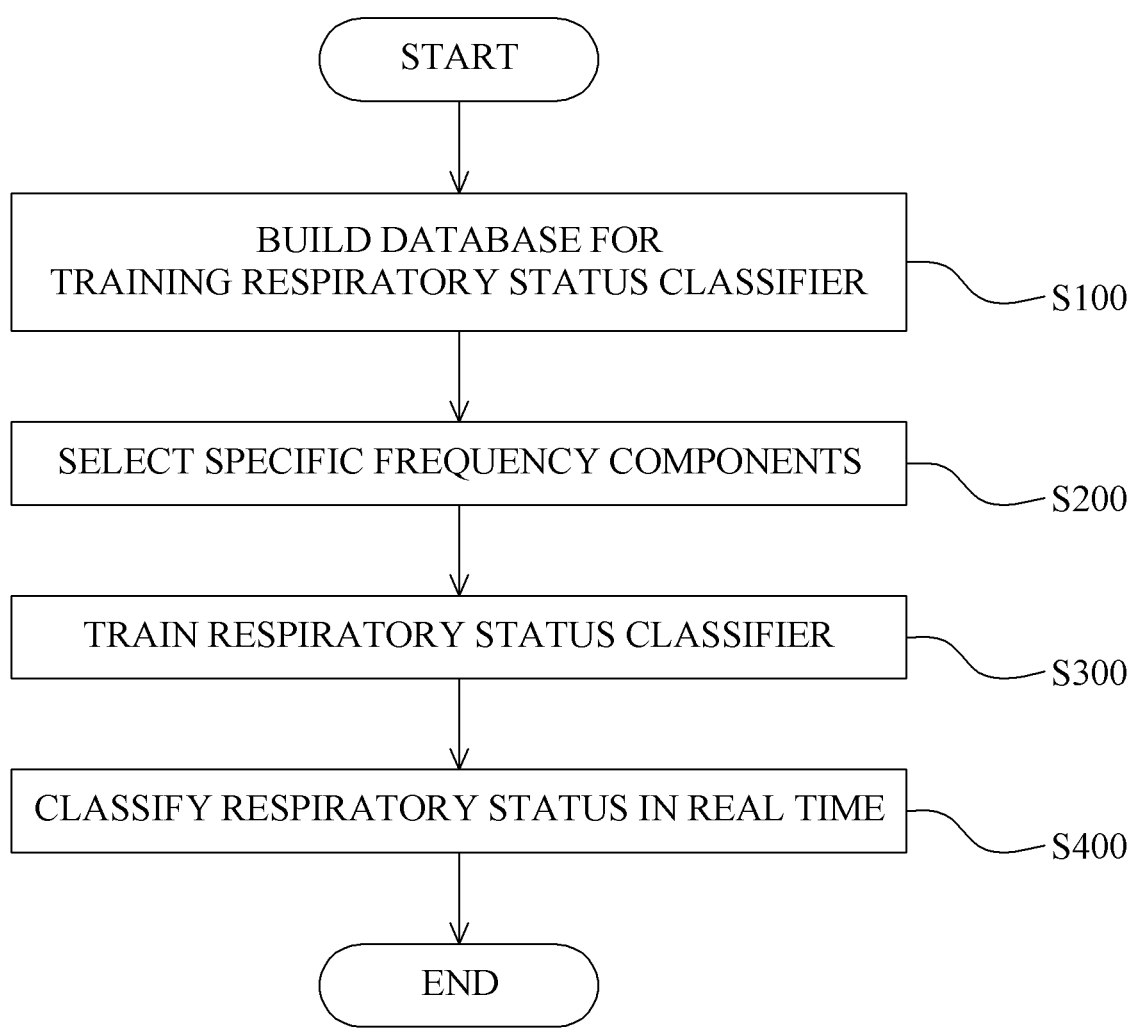
FIG. 1 is a flowchart schematically showing a method of generating a respiratory status classifier and a method of determining respiratory status using the generated respiratory status classifier according to an exemplary embodiment of the present invention.
Figure 2:
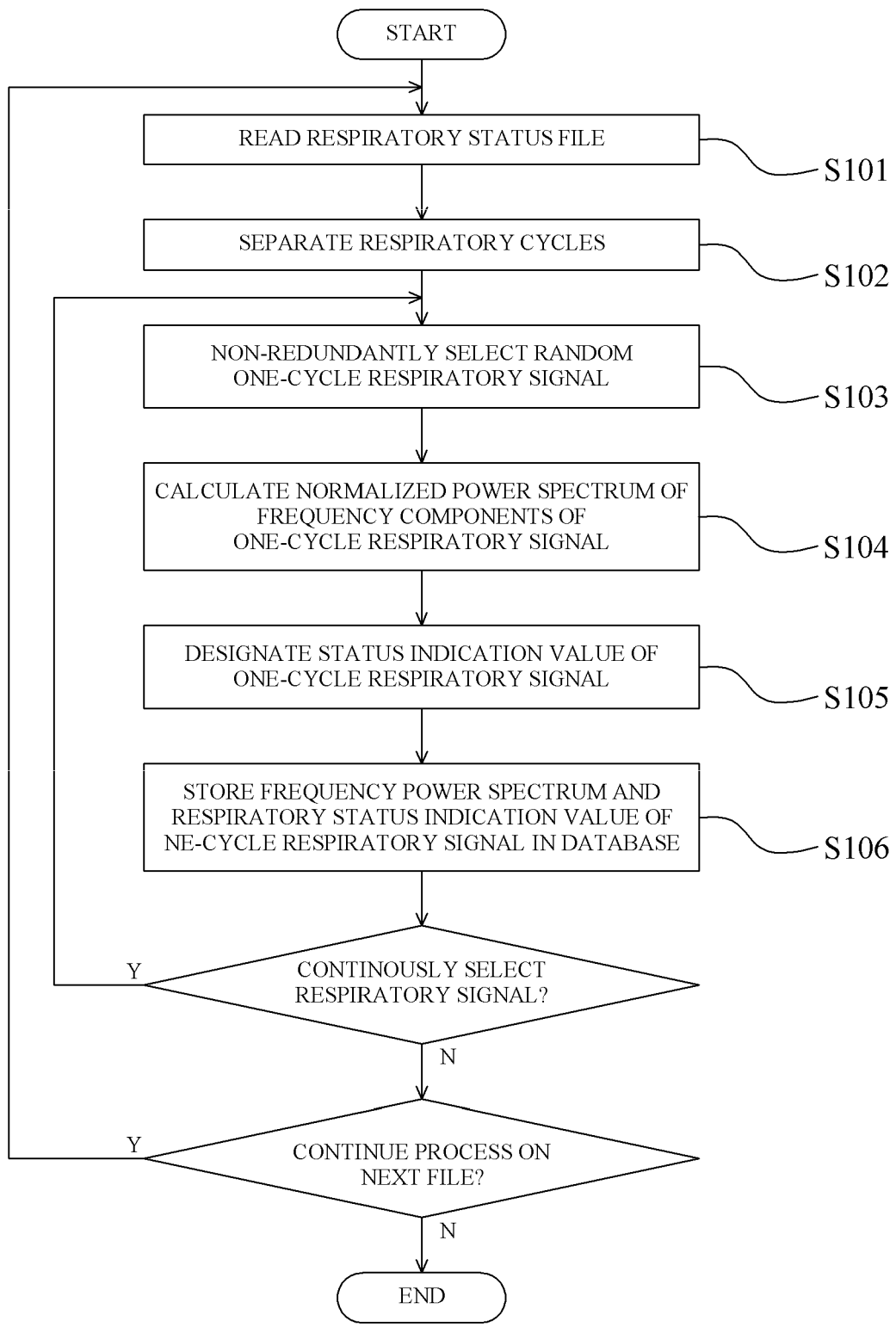
FIG. 2 is a flowchart showing an operation of building a training database for generating a respiratory status classifier according to an exemplary embodiment of the present invention.
Figure 3:
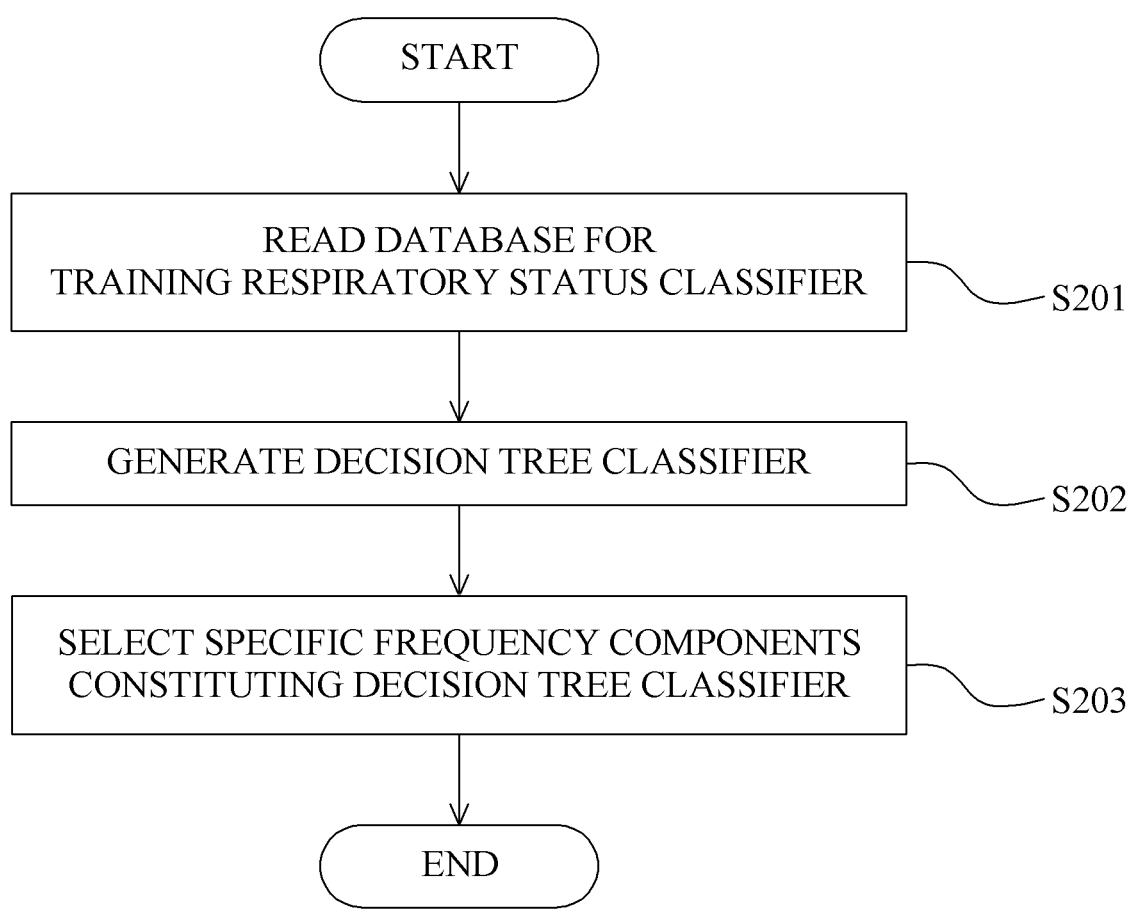
FIG. 3 is a flowchart showing an operation of selecting specific frequency components which are valid for respiratory status determination from among frequency components of a one-cycle respiratory signal according to an exemplary embodiment of the present invention.

FIG. 1 is a flowchart schematically showing a method of training a respiratory status classifier according to an exemplary embodiment of the present invention, FIG. 2 is a flowchart schematically showing an operation of transforming a respiratory sound signal into a frequency domain signal in the method of training a respiratory status classifier according to the exemplary embodiment of the present invention, and FIG. 3 is a flowchart schematically showing an operation of training a respiratory status classifier in the method of training a respiratory status classifier according to the exemplary embodiment of the present invention.

Referring to FIG. 1, the method of training a respiratory status classifier according to the exemplary embodiment of the present invention may include an operation of segmenting respiratory cycles (S101), an operation of generating a first group (S103), an operation of setting up status indices (S105), an operation of transforming a signal into a frequency domain signal (S107), an operation of generating a second group (S109), an operation of selecting specific frequency components (S111), and an operation of training a respiratory status classifier (S113).

In the operation of segmenting respiratory cycles (S101), a plurality of collected respiratory sound signals are segmented into respiratory cycles.

For example, the respiratory sound signals are collected in the form of recording files in which sleep breathing sounds of a plurality of people are recorded.

A respiratory cycle is a cycle in which a person inhales and exhales. Any algorithm for segmenting respiratory cycles from a respiratory sound signal may be used without limitation to segment respiratory cycles of the collected respiratory sound signals.

In the operation of generating a first group (S103), a set of respiratory cycles are randomly selected from among the segmented respiratory cycles, and a first group including the selected respiratory cycles is generated.

When all respiratory cycles of the collected respiratory sound signals are used to train a respiratory status classifier, it is necessary to calculate an excessive amount of data so as to train the respiratory status classifier. Therefore, the size of a data set for training the respiratory status classifier is reduced by generating the first group including respiratory cycles randomly selected from among the segmented respiratory cycles such that the amount of calculation performed to train the respiratory status classifier may be reduced.

In the operation of setting up status indices (S105), status indices each corresponding to the respiratory cycles included in the first group are set up.

For example, a status index of a snoring state, an apnea state, or a normal state may be set for each of the respiratory cycles included in the first group.

In the operation of transforming a signal into a frequency domain signal (S107), a respiratory sound signal of each of the respiratory cycles included in the first group is transformed into a frequency domain signal.

The operation of transforming a signal into a frequency domain signal (S107) will be described in detail with reference to FIG. 2. The operation of transforming a signal into a frequency domain signal (S107) may include an operation of performing a Fourier transform (S201), an operation of calculating power spectrums (S203), and an operation of normalizing the power spectrums (S205).

In the operation of performing a Fourier transform (S201), a Fourier transform is performed on each of the respiratory cycles included in the first group.

Since the collected respiratory sound signals represent an intensity level of a respiratory sound in the time domain, it is possible to transform the collected respiratory sound signals into frequency domain signals by performing a Fourier transform on the collected respiratory sound signals.

In the operation of calculating power spectrums (S203), power spectrums of respective frequency components included in the respiratory cycles on which a Fourier transform has been performed are calculated. It is possible to calculate power spectrums of respective frequency components included in respiratory cycles which have been transformed into frequency domain signals.

In the operation of normalizing the power spectrums (S205), the power spectrums of the respective frequency components included in the respiratory cycles are normalized.

In the operation of generating a second group (S109), a second group including the respiratory cycles which have been transformed into frequency domain signals is generated.

In addition to the frequency components and the power spectrums of the respective frequency components, the respiratory cycles included in the second group include the status indices set in the operation of setting up status indices each corresponding to the respiratory cycles (S105).

In the operation of selecting specific frequency components (S111), specific frequency components are selected from among the frequency components included in the respiratory cycles included in the second group.

In other words, it is possible to select frequency components which provide best discriminative power for classifying the respiratory cycles included in the second group according to the status indices set for the respective respiratory cycles from among the frequency components included in the respiratory cycles.

For example, a decision tree may be used to select specific frequency components. When a decision tree is generated on the basis of the frequency components included in the respiratory cycles included in the second group and the power spectrums of the respective frequency components, the respiratory cycles included in the second group may be classified according to the status indices set for the respective respiratory cycles.

Branch nodes (nodes except leaf nodes) of the generated decision tree may include frequency components and power spectrums of the frequency components as conditions for classifying the respiratory cycles included in the second group according to the status indices set for the respective respiratory cycles.

For example, the root node of the decision tree may include a condition asking whether a power spectrum of a 537 Hz frequency component is greater than 27, and each child node of the root node may include a condition asking whether a power spectrum of a 27 Hz frequency component is greater than 10 and a condition asking whether a power spectrum of 2116 Hz frequency component is greater than 15.

Also, identical frequency components may be recurrently included in branch nodes to increase the purity of the decision tree. For example, a branch node other than the root node may include a condition asking whether a 537 Hz frequency component is greater than 10.

Finally, frequency components included in branch nodes of the generated decision tree may be selected as specific frequency components for segmenting the respiratory cycles included in the second group.

In the exemplary embodiment of the present invention, an example of using a decision tree as a classification algorithm for classifying respiratory cycles included in a second group according to status indices set for the respective respiratory cycles. However, the classification algorithm used to classify respiratory cycles is not limited to a decision tree, and any algorithm for classifying respiratory cycles according to set status indices may be used without limitation.

In the operation of training the respiratory status classifier (S113), the respiratory status classifier is trained on the basis of the status indices set for the respective respiratory cycles included in the second group and the specific frequency components selected from among the frequency components included in the respective respiratory cycles.

The operation of training the respiratory status classifier (S113) will be described in detail with reference to FIG. 3. The operation of training the respiratory status classifier (S113) may include an operation of feeding an input to the respiratory status classifier (S301), an operation of calculating the number of errors (S303), and an operation of adjusting a parameter (S305).

In the operation of feeding an input to the respiratory status classifier (S301), the specific frequency components included in the respiratory cycles included in the second group, the power spectrums of the respective specific frequency components, and the status indices set for the respective respiratory cycles are input to the respiratory status classifier.

In the method of training a respiratory status classifier according to the exemplary embodiment of the present invention, the number of data sets used for training the respiratory status classifier is reduced through both the operation of generating a first group (S103) and the operation of selecting specific frequency components (S111), thus the amount of calculation required for a respiratory status classifier training process is reduced.

In the operation of calculating the number of errors (S303), the number of errors is calculated from output values from the respiratory status classifier.

The respiratory status classifier outputs any one of a normal state, a snoring state, and an apnea state as results on the basis of the input specific frequency components included in the respective respiratory cycles and the power spectrums of the respective specific frequency components.

The output values from the respiratory status classifier regarding the respective respiratory cycles are compared with the status indices set for the respective respiratory cycles. When the output values are not identical to the status indices, it is determined that an error has occurred, and the number or errors occurring in all the respiratory cycles included in the second group may be calculated.

For example, when a status index set for a first respiratory cycle is a normal state but output values from the respiratory status classifier is a snoring state, it is possible to determine that an error has occurred.

In the operation of adjusting a parameter (S305), when the calculated number of errors exceeds a preset error number, parameters of the respiratory status classifier is adjusted.

For example, when the number of errors calculated in first training is 100 and the preset error number is 50, the number of errors calculated in the first training exceeds the preset error number. Therefore, parameters of the respiratory status classifier may be adjusted so that the number of errors calculated in second training may be reduced.

After the parameters are adjusted, the operation of feeding an input to the respiratory status classifier (S301) to the operation of adjusting a parameter (S305) may be repeatedly performed until the number of calculated errors becomes less than or equal to the preset error number.

For example, after the parameters are adjusted as a result of the first training, the specific frequency components of the respiratory cycles included in the second group, the power spectrums of the specific frequency components, and the status indices set for the respective respiratory cycles may be input to the respiratory status classifier whose parameters have been adjusted. When the number of errors calculated as a result of second training exceeds the preset error number, the parameters of the respiratory status classifier are adjusted again, and third training may be performed. When the number of errors calculated as a result of $N^{th}$ training is equal to or less than the preset error number, training of the respiratory status classifier is finished.

Figure 4:
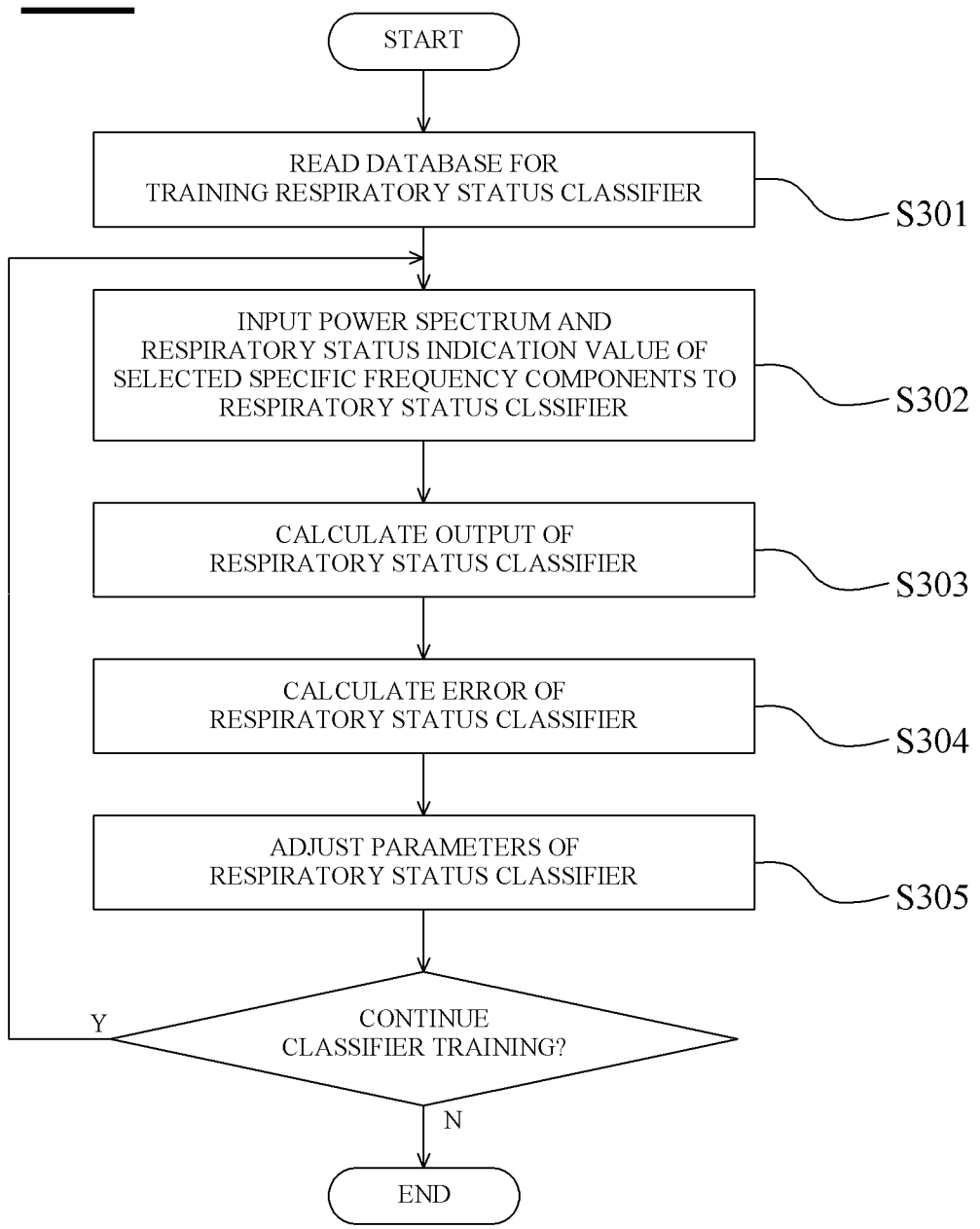
FIG. 4 is a flowchart showing an operation of training a respiratory status classifier according to an exemplary embodiment of the present invention.

FIG. 4 is a flowchart showing a method of determining respiratory status according to an exemplary embodiment of the present invention.

Referring to FIG. 4, the method of determining respiratory status according to the exemplary embodiment of the present invention may include an operation of segmenting respiratory cycles (S401), a operation of transforming a signal into a frequency domain signal (S403), an operation of calculating power spectrums (S405), an operation of feeding an input to a respiratory status classifier (S407), and an operation of determining respiratory status (S409).

In the operation of segmenting respiratory cycles (S401), the respiratory cycles of the collected respiratory sound signals are segmented. Any algorithm for segmenting the collected respiratory sound signals into respiratory cycles may be used without limitation.

In the operation of transforming a signal into a frequency domain signal (S403), a respiratory sound signal of each segmented respiratory cycle is transformed into a frequency domain signal.

Since the segmented respiratory cycles are respiratory sound signals in the time domain, it is possible to transform the respiratory sound signals into frequency domain signals by performing a Fourier transform on the cycle-segmented respiratory sound signals.

In the operation of calculating power spectrums (S405), power spectrums of specific frequency components are calculated among frequency components included in each of the respiratory cycles which have been transformed into the frequency domain signals.

The specific frequency components are identical to the specific frequency components which are selected when the respiratory status classifier is trained according to the method of training a respiratory status classifier. Only power spectrums of specific frequency components for best determining (i.e., classifying) respiratory status are calculated from among the frequency components included in the respiratory cycles transformed into the frequency domain signals.

In other words, in the method of determining respiratory status according to the exemplary embodiment of the present invention, only specific frequency components which are most suitable for determining the respiratory status of respiratory cycles are used to determine respiratory status. Therefore, it is possible to reduce the probability of misclassification caused by external noise, and the amount of data to be processed is reduced such that respiratory status may be rapidly determined.

In the operation of feeding an input to the respiratory status classifier (S407), the specific frequency components included in the respective respiratory cycles and the power spectrums of the respective specific frequency components are input to the respiratory status classifier trained according to the respiratory status classifier training method.

Throughout this specification, the terms "include," "have," or the like, when used herein, specify the presence of corresponding elements, features, and steps but do not preclude the presence or addition of one or more elements, features, steps, and equivalents thereof.

As used herein, the singular form includes the plural form unless the context clearly indicates otherwise. In other words, an element and the like mentioned herein may indicate the presence or addition of one or more other elements and the like.

Unless otherwise defined, all terms including technical and scientific terms used herein have the same meaning as commonly understood by those of ordinary skill in the technical field to which the present invention pertains.

In other words, terms, such as those defined in commonly used dictionaries, should be interpreted as having a meaning that is consistent with their meaning in the context of the relevant art and are not to be interpreted in an idealized or overly formal sense unless expressly so defined herein.

Hereinafter, a method of generating a respiratory status classifier and a method of determining respiratory status using the generated respiratory status classifier according to an exemplary embodiment of the present invention will be described in detail with reference to the accompanying drawings.

Figure 5:
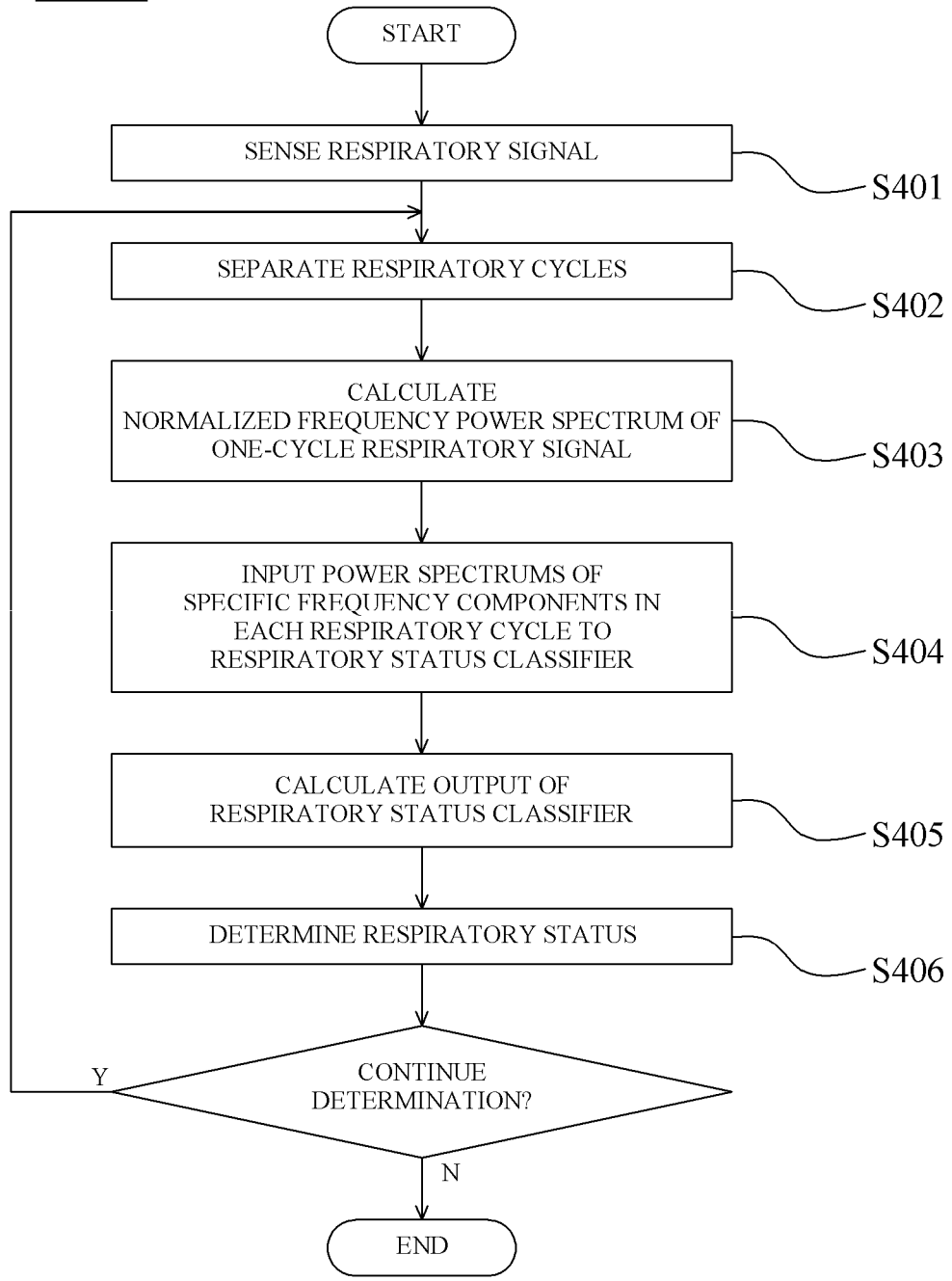
FIG. 5 is a flowchart showing an operation of determining respiratory status in real time using a generated respiratory status classifier according to an exemplary embodiment of the present invention.

FIG. 1 is a flowchart schematically showing a method of generating a respiratory status classifier and a method of determining respiratory status using the generated respiratory status classifier according to an exemplary embodiment of the present invention, FIG. 2 is a flowchart schematically showing an operation of building a training database for generating a respiratory status classifier according to an exemplary embodiment of the present invention, FIG. 3 is a flowchart showing an operation of selecting specific frequency components which are valid for respiratory status determination from among frequency components of a one-cycle respiratory signal according to an exemplary embodiment of the present invention, FIG. 4 is a flowchart showing an operation of training a respiratory status classifier according to an exemplary embodiment of the present invention, and FIG. 5 is a flowchart showing an operation of determining respiratory status in real time using a generated respiratory status classifier according to an exemplary embodiment of the present invention.

Referring to FIG. 1, the method of generating a respiratory status classifier and the method of determining respiratory status using the generated respiratory status classifier according to the exemplary embodiment of the present invention may include an operation of building a database for training a respiratory status classifier (S100), an operation of selecting specific frequency components (S200), an operation of training a respiratory status classifier (S300), and an operation of classifying respiratory status in real time (S400).

In the operation of building a database for training a respiratory status classifier (S100), data to be used for generating a respiratory status classifier is collected, processed, and stored. This will be described in detail with reference to FIG. 2.

Referring to FIG. 2, the operation of building a database for training a respiratory status classifier (S100) may include an operation of reading a respiratory signal file (S101), an operation of segmenting respiratory cycles (S102), an operation of non-redundantly selecting a random one-cycle respiratory signal (S103), an operation of calculating a normalized power spectrum of the one-cycle respiratory signal (S104), an operation of designating a respiratory status indication value of the one-cycle respiratory signal (S105), and an operation of storing the power spectrum and the respiratory status indication value of the one-cycle respiratory signal in a database (S106).

In the operation of reading a respiratory signal file (S101), one of multiple sleep respiratory signal streaming files which have been previously collected in a separate way and stored in the database is read.

In the operation of segmenting respiratory cycles (S102), one respiratory cycle from a start point of breathing to an end point thereof (i.e., a start point of next breathing) is segmented from a long-lasting respiratory signal stream. The operation of segmenting respiratory cycles (S102) may include preprocessing processes, such as filtering, direct current component removal, and normalization, for improving signal quality. In the operation of segmenting respiratory cycles (S102), it is possible to use any method for segmenting one cycle of breathing.

In the operation of non-redundantly selecting a random one-cycle respiratory signal (S103), a random one-cycle respiratory signal is selected so as not to overlap a previously selected one-cycle respiratory signal from a long-lasting respiratory signal stream consisting of numerous one-cycle respiratory sections which have been separated in the operation of separating respiratory cycles (S102).

In the operation of calculating a normalized power spectrum of the one-cycle respiratory signal (S104), a power spectrum is calculated by transforming the one-cycle respiratory signal, which has been selected in the operation of non-redundantly selecting a random one-cycle respiratory signal (S103), into the frequency domain by a Fourier transform, and an appropriate normalization method is applied to the power spectrum. The purpose of normalization is to remove factors which negatively affect the accuracy of respiratory status determination due to the intensity of a collected original signal varying according to environments in which a sleep respiratory signal is sensed, and it is possible to use any normalization method for achieving this purpose without limitation.

In the operation of designating a respiratory status indication value of the one-cycle respiratory signal (S105), the respiratory status of the one-cycle respiratory signal is designated according to a preset criterion. The respiratory status indication value includes an indication value of a normal respiratory state, a snoring state, or an apnea state and may further include an indication value indicating a level of the snoring state or apnea state.

For example, the preset criterion for designating a respiratory status indication value may be a criterion in which a person hears the sound of a one-cycle respiratory signal and designates a respiratory status indication value or a criterion in which a machine automatically makes determinations and designates respiratory status indication values which indicate the respiratory status of one-cycle respiratory signals.

A determination by a machine may be made by, for example, a sound intensity measuring device or an existing respiratory status classifier. In this case, respiratory signal status may be classified into normal breathing, snoring, and apnea, and for example, snoring may be subdivided into several levels from light snoring to heavy snoring. Also, respiratory status indication values of respiratory signals may be numbers, words, symbols, or the like.

In the operation of storing the power spectrum of frequency components and the respiratory status indication value of the one-cycle respiratory signal in a database (S106), a data entry in which the normalized power spectrum of frequency components and the respiratory status indication value for the selected one-cycle respiratory signal are paired is stored in the database.

The operation of non-redundantly selecting a random one-cycle respiratory signal (S103) to the operation of storing the power spectrum of frequency components and the respiratory status indication value of the one-cycle respiratory signal in a database (S106) may be repeated until it is no longer required to select a one-cycle respiratory signal from the single file.

In other words, when a pair of a power spectrum of frequency components and a respiratory status indication value is obtained from a respiratory signal corresponding to one cycle, a respiratory signal corresponding to a subsequent cycle (one cycle other than the cycle of the previously selected one-cycle respiratory signal) is selected (S103), a normalized power spectrum of the selected respiratory signal is calculated (S104), a respiratory status indication value of the selected respiratory signal is designated (S105), and a pair of the power spectrum and the respiratory status indication value of the respiratory signal corresponding to the subsequent cycle is stored in the database.

When a required number of data pairs of a power spectrum and a respiratory status indication value are obtained from a plurality of respiratory signals corresponding to individual cycles, another sleep respiratory signal streaming file is read. Subsequently, operations S102 to S106 are repeated for the other sleep respiratory signal streaming file.

The operation of reading a respiratory signal file (S101) to the operation of storing the power spectrum of frequency components and the respiratory status indication value of the one-cycle respiratory signal in a database (S106) are repeated until it is no longer required to process a new respiratory signal file.

In other words, in the operation of building a database for training a respiratory status classifier (S100), a process of acquiring a data pair of a power spectrum of frequency components and a respiratory status indication value of a respiratory signal corresponding to one respiratory cycle may be performed, and a process of acquiring a data pair from each of respiratory signals corresponding to other respiratory cycles may be repeatedly performed until a specific condition of no longer being required to select a one-cycle respiratory signal from a single file is satisfied. When data pairs are acquired from one file until the specific condition is satisfied, a process of acquiring data pairs from a subsequent respiratory signal file may be repeatedly performed until it is no longer required to process a new respiratory signal file.

For example, the specific condition is a case where the number of data pairs acquired from one file for each respiratory status should satisfy a preset maximum number. When the preset number of data pairs are acquired from one file for each respiratory status (the specific condition is satisfied), the repeated process on the file may be finished.

In the operation of selecting specific frequency components (S200), only some frequency components containing information which is valid for respiratory status determination are selected from among frequency components included in a one-cycle respiratory signal. This will be described in detail with reference to FIG. 3.

Referring to FIG. 3, the operation of selecting specific frequency components (S200) may include an operation of reading a database for training a respiratory status classifier (S201), an operation of generating a decision tree classifier (S202), and an operation of selecting specific frequency components (S203).

In the operation of reading a database for training a respiratory status classifier (S201), the database for classifier training built in the operation of building a database for training a respiratory status classifier (S100) is read.

In the operation of generating a decision tree classifier (S202), a decision tree classifier is generated using data read from the database for training a respiratory status classifier. A decision tree classifier may be generated to perform classification using frequency components included in data pairs as input characteristics and power spectrum values of the frequency components as values of the input characteristics.

A decision tree classifier visually shows a decision making process in a clear manner and may be represented in the shape of an upside-down tree. A classification is made along a path extending from a root node to a leaf node through internal nodes.

Each of the branch-node including the root node and one or more internal nodes of the decision tree corresponds to one input feature (in the case of the present invention, a frequency component), and each of branches connected to nodes of next stages corresponds to a condition of a value that an input feature corresponding to a current node may have (in the case of the present invention, a range of a power spectrum value of a frequency component or one of several power spectrum values). A leaf node corresponds to one of the classification categories (e.g., three categories of normal respiratory state, snoring state, and apnea state indicated by the respiratory status indication values).

Generating a decision tree classifier includes an operation of finding an input feature of a corresponding node and a condition of an input feature value so that a data set given to one node may be optimally classified, an operation of expanding branches corresponding to the condition of the input feature value and nodes in the next stage, and an operation of distributing a subset of data satisfying the condition of the input feature value corresponding to a branch to a node of the next stage expanded along the branch. Such an expansion and data distribution process is repeated in each node such that a tree structure is expanded. In other words, a decision tree classifier may be generated by classifying data pairs according to designated respiratory status indication values until a misclassification rate of data pairs classified according to respiratory status indication values is below a preset rate. When a misclassification rate of an expanded node is below the preset rate, the node becomes a leaf node.

In the method of generating a decision tree classifier according to the exemplary embodiment of the present invention, input feature of data are frequency components, and a condition of a value corresponds to a range of a power spectrum value of a corresponding frequency component.

For example, when the root node or one internal node has the optimal binary classification criterion "is a power spectrum value of a $205^{th}$ frequency component greater than 27?" due to the input feature and the input feature value "a power spectrum value of a $205^{th}$ frequency component" and the condition of a value "greater than 27," two nodes of the next stage are formed by expanding one branch corresponding to the condition "greater than 27" and another branch corresponding to the condition "less than or equal to 27," and a subset of data greater than 27 and a subset of data less than or equal to 27 are separately distributed to the two nodes of the next stage corresponding to the conditions.

When a data set allocated to a newly expanded node satisfies the specific condition, the node is designated as a leaf node, and a classification category is designated according to the attribute of the data set. For example, the specific condition may be set to "a proportion of elements belonging to one classification region exceeds a certain level."

In the operation of selecting specific frequency components (S203), only frequency components corresponding to the root node and internal nodes included in a complete decision tree are selected as new input feature. In general, the number of frequency components shown in nodes of the decision tree is much less than the total number of frequency components, and the selected input characteristics may be construed as providing information which is sufficient and valid for data classification.

In other words, frequency components included as input feature in the root node and the internal nodes of the complete decision tree are selected as specific frequency components.

In the operation of training a respiratory status classifier (S300), the respiratory status classifier is trained using data which has only the specific frequency components selected in the operation of selecting specific frequency components (S200) as input feature This will be described in detail with reference to FIG. 4.

Referring to FIG. 4, the operation of training a respiratory status classifier (S300) may include an operation of reading the database for training a respiratory status classifier (S301), an operation of inputting a power spectrum of the selected frequency components and a respiratory status indication value to the respiratory status classifier (S302), an operation of calculating an output of the respiratory status classifier (S303), an operation of calculating an error of the respiratory status classifier (S304), and an operation of adjusting parameters of the respiratory status classifier (S305).

In the present invention, a type of respiratory status classifier is not specified, and it is possible to use any classifier for outputting respiratory status using a power spectrum value as an input. For example, a Bayesian classifier, a multi-layer perceptron (MLP) classifier, a support vector machine (SVM), or the like may be used as a respiratory status classifier. In the present invention, a decision tree which is a classifier is used to select a specific frequency component.

In the operation of reading the database for training a respiratory status classifier (S301), data stored in the database for training a respiratory status classifier built in the operation of building a database for training a respiratory status classifier (S100) is read. In the built database for classifier training, power spectrums and respiratory status indication values of one-cycle respiratory signals are stored in pairs, and the data is used to train the respiratory status classifier.

In the operation of inputting a power spectrum of the selected frequency components and a respiratory status indication value to the respiratory status classifier (S302), a power spectrum of the frequency components and a respiratory status indication value selected by the decision tree classifier in the operation of selecting specific frequency components (S200) are input to the respiratory status classifier. Details of the inputs may be determined according to characteristics of the respiratory status classifier.

In the operation of calculating an output of the respiratory status classifier (S303), an output value of the classifier is calculated for the input data. A method of calculating an output value is determined according to the classifier.

In the operation of calculating an error of the respiratory status classifier (S304), a difference between the output value of the classifier and the respiratory status indication value is calculated. It is possible to use any calculation method and formula reflecting the definition (concept) of an error caused by the difference.

For example, an MLP classifier may be used as the respiratory status classifier. In this case, when a respiratory status indication value is expressed as the vector $\vec{t}=[t_1\ t_2\ \ldots\ t_c]'$ and an output value is expressed as the vector $\vec{o}=[o_1\ o_2\ \ldots\ o_c]'$ with respect to one piece of input data p, the error may be calculated by the following equation which reflects a difference between the two vectors.

$$E_p = \frac{1}{2}\sum_{i=1}^{c}(t_i - o_i)^2$$

Also, an error of the total of n samples of data used for training may be calculated by the following equation which sums up squared errors of the respective samples of data.

$$E = \sum_{p=1}^{n} E_p = \frac{1}{2}\sum_{p=1}^{n}\sum_{i=1}^{c}(t_i - o_i)^2$$

In the operation of adjusting parameters of the respiratory status classifier (S305), values of parameters which characterize the classifier are adjusted so that errors of the classifier may be minimized. A method of adjusting parameters is determined according to the type of classifier.

The operation of inputting a power spectrum of the selected frequency components and a respiratory status indication value to the respiratory status classifier (S302) to the operation of adjusting parameters of the respiratory status classifier (S305) may be repeatedly performed until a preset condition for stopping training is satisfied. The condition for stopping training may vary according to a detailed training method for the respiratory status classifier and a setting made by a user.

As an example of the condition for stopping training, in the case of an MLP, repeated training is stopped when training is repeated a preset number of times or an error which has occurred becomes less than or equal to a preset reference.

In the operation of classifying respiratory status in real time (S400), respiratory status is determined for respiratory signals of respective respiratory cycles of a continuously input respiratory signal streaming using the respiratory status classifier which has been trained in the operation of training a respiratory status classifier (S300). This will be described in detail with reference to FIG. 5.

Referring to FIG. 5, the operation of classifying respiratory status in real time (S400) may include an operation of sensing a respiratory signal using a device such as a microphone (S401), an operation of segmenting respiratory cycles (S402), an operation of calculating a normalized power spectrum of a one-cycle respiratory signal (S403), an operation of inputting a power spectrum of selected frequency components to the respiratory status classifier (S404), an operation of calculating an output of the respiratory status classifier (S405), and an operation of determining respiratory status (S406).

In the operation of sensing a respiratory signal (S401), a continuous respiratory signal stream is sensed in real time by a device for sensing sound of breathing such as a microphone.

In the operation of segmenting respiratory cycles (S402), one respiratory cycle from a start point of breathing to an end point thereof (i.e., a start point of next breathing) is segmented from a respiratory signal stream which is sensed in real time. The operation of segmenting respiratory cycles (S402) is functionally identical to the operation of segmenting respiratory cycles (S102) in the operation of building a database for training a respiratory status classifier (S100).

In the operation of calculating a normalized power spectrum of a one-cycle respiratory signal (S403), a power spectrum is calculated by transforming a selected one-cycle respiratory signal into the frequency domain by a Fourier transform, and an appropriate normalization method is applied to the power spectrum. The operation of calculating a normalized frequency spectrum of an one-cycle respiratory signal (S403) is functionally identical to the operation of calculating a normalized power spectrum of a one-cycle respiratory signal (S104) in the operation of building a database for training a respiratory status classifier (S100).

In the operation of inputting power spectrum of selected frequency components to the respiratory status classifier (S404), power spectrums of specific frequency components selected by the decision tree classifier generated in the operation of selecting specific frequency components (S200) are provided to the respiratory status classifier. The operation of inputting power spectrum of selected frequency components to the respiratory status classifier (S404) is identical to an operation of inputting only power spectrums without respiratory status indication values in the operation of inputting power spectrums and respiratory status indication values of the selected frequency components to the respiratory status classifier (S302).

In the operation of calculating an output of the respiratory status classifier (S405), an output value of the respiratory status classifier is calculated from inputs of the power spectrums. The operation of calculating an output of the respiratory status classifier (S405) is functionally identical to the operation of calculating an output of the respiratory status classifier (S303) in the operation of training a respiratory status classifier (S300).

In the operation of determining respiratory status (S406), respiratory status is determined to be a normal respiratory state, a snoring state, or an apnea state according to the output of the respiratory status classifier.

The operation of segmenting respiratory cycles (S402) to the operation of determining respiratory status (S406) may be continuously repeated for continuously input respiratory signals.

In a method of generating a respiratory status classifier and a method of determining respiratory status using the generated respiratory status classifier according to an exemplary embodiment of the present invention, only some specific frequency components providing high discriminative power for respiratory status classification are selectively used among frequency components of each segmented respiratory cycle. Therefore, it is possible to reduce the probability of incorrectly classifying respiratory status due to external noise.

Also, since only some specific frequency components are selectively extracted from respiratory cycle-segmented respiratory signals and used, it is possible to reduce the computational time required for training a respiratory status classifier in order to generate a respiratory status classifier as well as the computation required for actually determining respiratory status using the generated respiratory status classifier. Accordingly, even when a computer or another device for operating the classification algorithm has relatively low performance, it is possible to determine respiratory status rapidly and accurately.

Although the present invention has been described with some exemplary embodiments, various modifications or variations can be made within the scope defined by the claims stated below. The technical scope of the present invention should be determined by the following claims.

What is claimed is:

1. A method of generating a respiratory status classifier, the method comprising:
    segmenting collected respiratory signals according to respiratory cycles such that each segment includes respiratory signals having a same respiratory cycle, wherein a respiratory cycle is a cycle in which a person inhales and exhales;
    acquiring power spectrums of frequency components for the respiratory signals corresponding to a plurality of selected respiratory cycles among the segmented respiratory signals;
    acquiring a data pair of a power spectrum of frequency components and a designated respiratory status indication value for each respiratory signal corresponding to the plurality of selected respiratory cycles;
    generating a decision tree classifier for classifying the respiratory signals corresponding to one respiratory cycle according to the respiratory status indication values using the frequency components included in the data pair as input feature and using the power spectrum value of the frequency components as values of the input feature;
    selecting only frequency components constituting a root node and an internal node of the generated decision tree classifier as specific frequency components;
    and
    training the respiratory status classifier using data pairs of a power spectrum value of the selected specific frequency components and the designated respiratory status indication value.

2. The method of claim 1, wherein the acquiring of data pairs is performed on one of the collected respiratory signals and then repeatedly performed on other respiratory signals until a specific condition is satisfied.

3. The method of claim 1, wherein the acquiring of data pairs comprises:
    calculating a power spectrum of frequency components for a respiratory signal corresponding to one respiratory cycle and designating a respiratory status indication value for the one respiratory signal corresponding to the one respiratory cycle to acquire a data pair of the respiratory signal corresponding to the one respiratory cycle; and
    until a specific condition is satisfied, repeatedly acquiring a data pair of each of respiratory signals corresponding to others respiratory cycles except the one respiratory cycle whose data pair has been acquired.

4. The method of claim 1, wherein the acquiring of the power spectrums comprises normalizing values of the power spectrums of the frequency components.

5. The method of claim 1, wherein the respiratory status indication value includes an indication value of a normal respiratory state, a snoring state, or an apnea state.

6. The method of claim 1, wherein the respiratory status indication values further include indication values for representing a level of the snoring state and a level of the apnea state in numbers, text, or symbols.

7. The method of claim 1, wherein the generating of a decision tree classifier comprises generating the decision tree classifier by repeatedly expanding the single internal node according to respiratory status indication values designated for data pairs allocated to the internal node until a ratio of data pairs belonging to one respiratory status to the data pairs becomes a preset ratio.

8. The method of claim 1, wherein the training of the respiratory status classifier comprises:
    inputting the power spectrums of the selected specific frequency components and the designated respiratory status indication values to the respiratory status classifier; and
    calculating errors by comparing output values from the respiratory status classifier with the designated respiratory status indication values, and adjusting parameters of the respiratory status classifier to reduce the calculated errors.

9. The method of claim 8, wherein the training of the respiratory status classifier is finished when the training is repeatedly performed a preset number of times or the calculated errors are below a preset reference.

10. A method of determining respiratory status, the method comprising:
    segmenting a one-cycle respiratory signal from collected respiratory signals;
    inputting power spectrums of the specific frequency components selected in claim 1 among power spectrums of the segmented one-cycle respiratory signal to the respiratory status classifier generated according to the method of claim 1; and
    determining respiratory status of the segmented one-cycle respiratory signal according to output values of the respiratory status classifier based on inputs.

11. The method of claim 10, further comprising, after the determining of respiratory status, repeating the segmenting of a one-cycle respiratory signal to the determining of respiratory status for a respiratory signal continuous to the segmented one-cycle respiratory signal.

* * * * *